United States Patent
Rothbart (12) 
(10) Patent No.: US 6,212,723 B1
(45) Date of Patent: Apr. 10, 2001

(54) FOOT SUPPORT SYSTEM AND USE IN SHOE LASTS

(75) Inventor: Brian A. Rothbart, Tacoma, WA (US)

(73) Assignee: GRD Biotech, Inc., Lakewood, WA (US)

( * ) Notice: Subject to any disclaimer, the term of this patent is extended or adjusted under 35 U.S.C. 154(b) by 0 days.

(21) Appl. No.: 09/413,042

(22) Filed: Oct. 6, 1999

Related U.S. Application Data (60) Division of application No. 09/031,258, filed on Feb. 26, 1998, now Pat. No. 6,092,314, which is a continuation-in-part of application No. 08/733,116, filed on Oct. 16, 1996, now abandoned.

(51) Int. Cl.⁷ .................................................. A43D 3/02
(52) U.S. Cl. .................................................. 12/133 R
(58) Field of Search ...................... 12/133 R, 133 B, 12/133 A, 136 R (56) References Cited

U.S. PATENT DOCUMENTS

| | | |
|---|---|---|
| 353,910 | 12/1886 | Zacharie . |
| 679,947 * | 8/1901 | Collins . |
| 841,732 * | 1/1907 | Smith . |
| 1,554,883 | 9/1925 | Sahlin . |
| 1,617,132 * | 2/1927 | Morin . |
| 1,756,587 * | 4/1930 | Durkee . |
| 1,847,973 | 3/1932 | Morton . |
| 2,052,115 | 8/1936 | Shulman . |
| 2,528,082 * | 10/1950 | Rubico . |
| 2,616,190 | 11/1952 | Darby . |
| 2,737,671 * | 3/1956 | Hill . |
| 3,663,978 * | 5/1972 | Meszaros . |
| 3,742,627 | 7/1973 | Schneider . |
| 4,360,027 | 11/1982 | Friedlander et al. . |
| 4,642,911 | 2/1987 | Talarico, II . |
| 4,676,801 | 6/1987 | Lundeen . |
| 5,058,585 | 10/1991 | Kendall et al. . |
| 5,327,663 | 7/1994 | Pryce . |
| 5,327,664 | 7/1994 | Rothbart . |
| 5,572,808 | 11/1996 | Birke . |

FOREIGN PATENT DOCUMENTS

| | | |
|---|---|---|
| 241398 | 7/1946 | (CH) . |
| 288914 | 6/1914 | (DE) . |
| 2 652 260 | 3/1991 | (FR) . |

OTHER PUBLICATIONS

James Natale, "Wedges and Corrections for Various Cases of Pronations", *The Master Shoe Rebuilder*, vol. X, No. 2 (Oct., 1950).

Brian A. Rothbart, D.P.M., Ph.D. and Lew Estabrook, D.C., "Excessive Pronation: A Major Biomechanical Determinant in the Development of Chondromalacia and Pelvic Lists", *Journal of Manipulative and Physiological Therapeutics*, vol. 11, No. 5, 373–379 (Oct., 1988).

Brian A. Rothbart, DPM, PhD, Kevin Hansen, PT, Paul Liley, DDS, and M. Kathleen Yerratt, RN, "Resolving Chronic Low Back Pain: The Foot Connection", *American Journal of Pain Management*, vol. 5, No. 3, 73 and 84–90 (Jul., 1995).

Brian A. Rothbart, DPM, PhD, and M. Kathleen Yerratt, RN, "An Innovative Mechanical Approach to Treating Chronic Knee Pain: A Bio–Implosion Model", *American Journal of Pain Management*, vol. 4, No. 3, 123–127 (Jul., 1994).

* cited by examiner

Primary Examiner—Ted Kavanaugh
(74) Attorney, Agent, or Firm—Christensen O'Connor Johnson Kindness PLLC (57) ABSTRACT

A foot support system (60) for supporting a hyperpronating foot (20) both dynamically while the foot (20) is in motion and statically is disclosed. The foot support system (60) is a bed upon which the foot (20) rests which includes an inner edge (62) and an outer edge (64). The foot support system (60) is positioned underneath the medial column of the forefoot of foot (20). The foot support system (60) laterally decreases in thickness from the inner edge (62) to the outer edge (64). The inner edge (62) is positioned along the medial side of the foot (20), and the outer edge (64) is positioned longitudinally in a zone adjacent to a lateral margin of the hallux (48), the proximal phalanx (46), and the first metatarsal (36) and a medial margin of the phalanges (47) of the second toe and the second metatarsal (38).

4 Claims, 10 Drawing Sheets

FOOT SUPPORT SYSTEM AND USE IN SHOE LASTS

RELATED CROSS REFERENCE

The following application is a divisional of a prior application Ser. No. 09/031,258, filed Feb. 26, 1998 now U.S. Pat. No. 6,092,314, which is a continuation-in-part of application Ser. No. 08/733,116, filed on Oct. 16, 1996 now abandoned.

FIELD OF THE INVENTION

This invention relates to foot support systems and, more particularly, to foot support systems for hyperpronating feet.

BACKGROUND OF THE INVENTION

Throughout the years people have been continuously searching for better ways to comfort their feet while walking. One common cause of discomfort associated with walking is hyperpronation of the feet. Hyperpronation is an inward, forward and downward twisting of the foot relative to the ground.

To treat and support a hyperpronating foot, foundational stability is provided by maximizing foot-to-ground contact so that the foot does not collapse. Traditionally, this is accomplished by orthotic devices. In particular, orthotics for supporting a hyperpronating foot are designed to support deficits in a foot's contact with the ground, and in essence function so as to build the ground up to the foot.

Presently, some orthotics wedge the forefoot from the medial side to the lateral side of the foot. Other orthotics similarly wedge the heel. It is believed that these orthotics, designed to prevent hyperpronation, sufficiently support the static foot. However, once the foot is in motion, pronation and discomfort often return. In some instances, this discomfort is partially attributed to the foot sliding off the orthotic during gait.

Therefore, there is a need for a foot support system that supports a hyperpronating foot both statically and dynamically.

SUMMARY OF THE INVENTION

The present invention is a foot support system for supporting a hyperpronating foot both statically and dynamically. The foot support system is essentially an elongate bed upon which a portion of the foot rests. The foot support system includes an inner edge, an outer edge, a front edge and a back edge. The inner edge is positioned along the medial side the foot, and the outer edge is positioned longitudinally in a zone adjacent to a lateral margin of the hallux, the proximal phalanx, and the first metatarsal of the foot and a medial margin of the phalanges of the second toe and the second metatarsal. The foot support system linearly decreases in thickness from the inner edge to the outer edge. The foot support system also extends from the front edge, which is positioned along an anterior end of the hallux, to the back edge, which is positioned between an anterior end of the talar head and an anterior end of the plantar portion of the heel.

In accordance with other aspects of the invention, the foot support system decreases in thickness from the inner edge to the outer edge in a concave, convex, or stepped fashion.

In accordance with still other aspects of this invention, the foot support system is, preferably, an orthotic.

In accordance with further other aspects of this invention, the foot support system also includes a plate having a uniform thickness which is shaped such that it follows the contour of the sole of the foot. Further, the plate is positioned either underneath or on top of the elongate bed of the foot support system, or, preferably, the plate and elongate bed are integrated to form a single unit. The foot support system integrating the plate and elongate bed into a single unit is an insole for inserting in a shoe.

In accordance with further aspects of this invention, the foot support system is integrated into a shoe bed of a shoe.

In accordance with still other aspects of this invention, the foot support system which is integrated into the shoe bed of a shoe is made from a last having a cavity corresponding to the foot support system such that a shoe formed around the last includes the foot support system in the shoe bed.

As will be readily appreciated from the foregoing description, the invention provides a foot support system that supports the medial column of the foot from the anterior end of the hallux to a position between the anterior end of the talar head and the anterior end of the plantar portion of the heel, and thus supports a foot having Rothbart's Foot Structure and prevents hyperpronation. Because the foot support system extends to the hallux, the foot is supported in its anatomical position not only while standing but also during toe-off while in motion. Therefore, the foot support system of the present invention more fully supports a hyperpronating foot and decreases discomfort associated therewith.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

The present invention is directed to a foot support system that supports a hyperpronating foot both statically and dynamically. Although some have theorized about the cause of hyperpronation, it has never been sufficiently understood. In order to adequately prevent hyperpronation and the discomfort associated therewith, however, such an understanding is necessary. In this regard, in order to better understand the present invention, a brief review of the embryological development of the lower limb bud and foot is necessary. This discussion will elucidate the spatial derangement of the foot and lead to the necessity for using the foot support system of the present invention.

Figure 1:
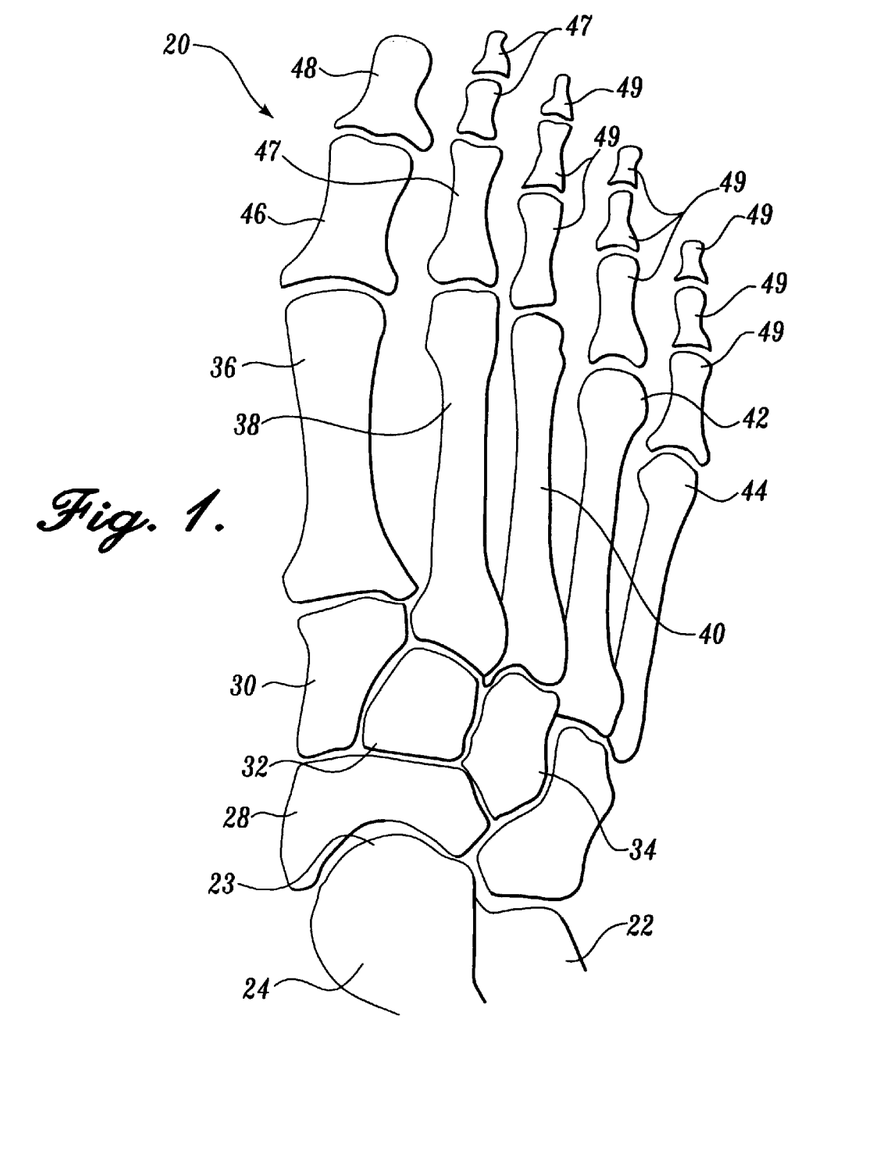
FIG. 1 is a top view of a foot depicting a plurality of bones in the foot.

For reference, FIG. 1 illustrates a plurality of bones in an adult foot 20. The bones shown in foot 20 include a calcaneus 22, a talus 24 having a talar head 23 and a talar neck, a navicular 28, a medial cuneiform 30, an intermediate cuneiform 32, a lateral cuneiform 34, a first metatarsal 36, a second metatarsal 38, a third metatarsal 40, a fourth metatarsal 42, a fifth metatarsal 44, a proximal phalanx 46, a hallux 48, a plurality of phalanges 47 of the second toe, and a plurality of phalanges 49 of the third, fourth and fifth toes. The hallux 48 and the proximal phalanx 46 are also referred to as the phalanges of the first toe.

Figure 2:
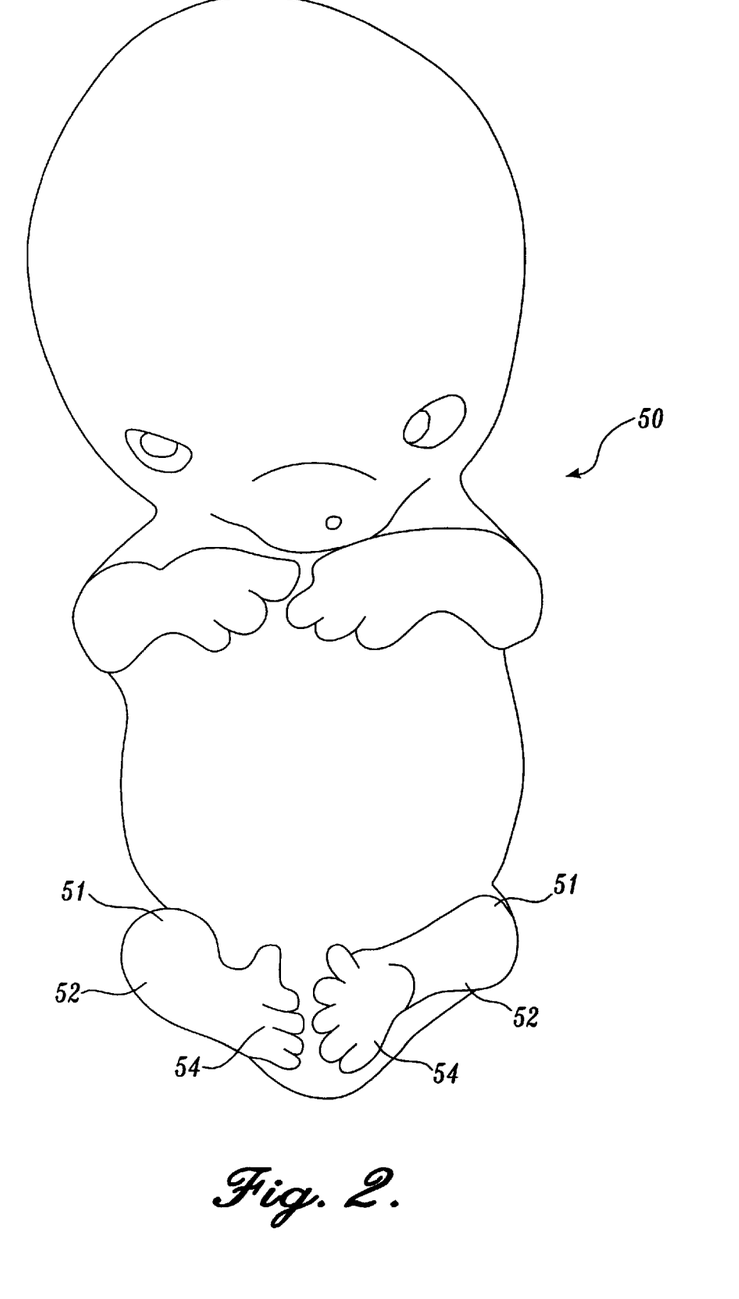
FIG. 2 is a perspective view of an embryo at 8 weeks post fertilization.

FIG. 2 illustrates a fetus 50 at the end of the embryonic period at 8 weeks post fertilization (pf). The fetus 50 has lower limbs, each corresponding to a thigh 51, a lower leg 52 and a foot 54. The lower limbs lie in a sagittal plane, as shown in FIG. 2. The lower limbs are externally rotated relative to the midline of the body such that the posterior side of the thighs and lower legs and the soles of the feet are facing one another. Furthermore, the foot 54 lies in an extreme plantarflexed position relative to the lower leg 52.

During foetal development, important axial rotational changes occur that alter the foot to leg relationship. Generally, there is a progressive internal rotation of the thigh-lower leg-foot segments which occurs in a sequential pattern. Initially, the thigh-lower leg segment internally rotates, the right thigh-lower leg segment rotating counter-clockwise and the left rotating clockwise. This positions the foot 54 so that it is plantarflexed and externally rotated relative to the lower leg 52.

Then, between 8 and 12 weeks pf, the foot undergoes dramatic reorientation. By week 9 pf, the ankle joint is forming, taking the foot out of its extreme plantarflexed position. The feet are still on the sagittal planes, soles facing each other. The resulting foot to lower leg relationship is termed supinatus. At week 10 pf, the foot begins to unwind, starting proximally at the heel and progressing distally through the inner arch and rest of the forefoot. Initially, the posterior surface of the calcaneus begins to untwist, the right heel bone in a counterclockwise direction and the left heel bone in a clockwise direction. Thus, the rearfoot is no longer in supinatus. For a brief period of time, the foot appears tortuously twisted, heel to ball. Shortly thereafter, the head and neck of the talus, also referred to as the talar head and neck, begin to untwist. This untwisting of the talus reduces the supinatus within the ball of the foot as the talar head carries the navicular, internal cuneiform, first metatarsal, proximal phalanx and hallux out of supinatus into their proper positions. By week 36 pf, the untwisting process is almost completed and the fetal foot resembles that of the adult foot. Furthermore, the foot supinatus is no longer apparent.

Figure 3:
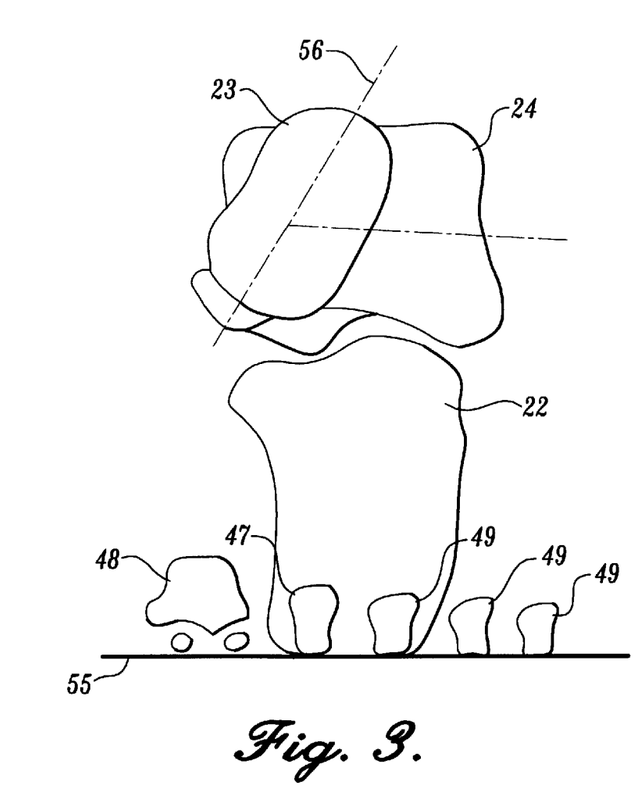
FIG. 3 is a front view of a mechanically stable adult foot.

FIG. 3 illustrates a front skeletal view of an adult foot which has fully completed the untwisting process. As shown in FIG. 3, the hallux 48, the phalanges 47 of the second toe, and the phalanges 49 of the third, fourth and fifth toes are in full contact with a ground level 55. Furthermore, the head 23 of the talus 24 is depicted in its completely unwound position. For reference, an axis 56 through the completely unwound talar head 23 forms approximately a 50 degree angle relative to the ground level 55.

However, if the talar head 23 does not untwist, the entire inside of the foot, excluding the heel, is affected. In 1906, R. S. Sewell, in *A study of the asragulus*, Part IV, J Anat Physiol 40:152, reported up to a 20 degree twist in the talar head, a condition he refers to as talar supinatus. Recently, the inventor has discovered the effect talar supinatus has on the navicular, internal cuneiform, first metatarsal, proximal phalanx and hallux, hereinafter, the medial column, relative to the other bones of the foot In this regard, the inventor has observed 35 mm of dorsal displacement of the medial column. The twist and dorsal displacement of the medial column is hereinafter referred to as Rothbart's Foot Structure.

Figure 4:
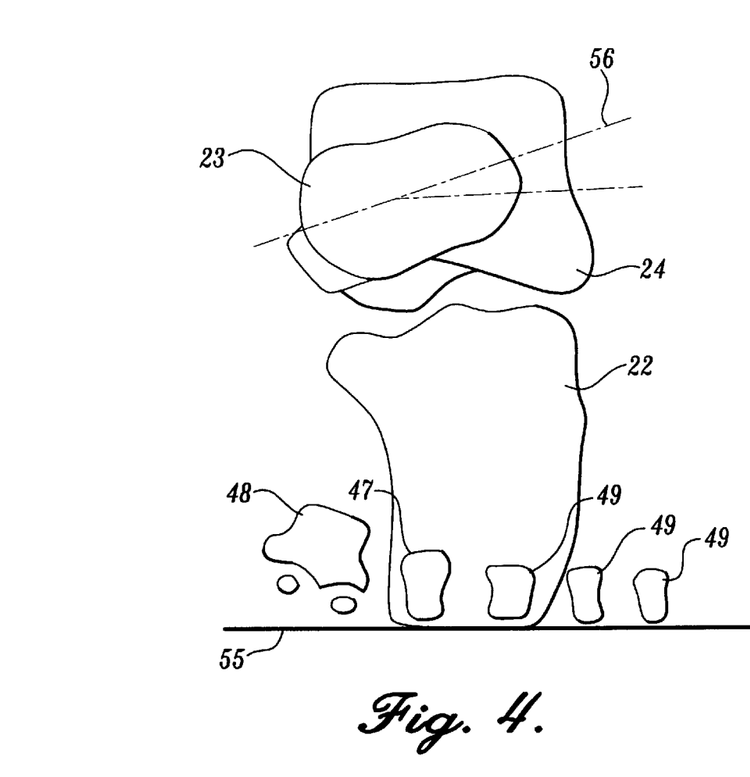
FIG. 4 is a front view of an adult foot having Rothbart's Foot Structure, depicting a twisted talar head and an elevated medial column of the foot.

FIG. 4 illustrates a front view of an adult foot which has not completed the untwisting process, thus having Rothbart's Foot Structure. As shown in FIG. 4, the phalanges 47 of the second toe and the phalanges 49 of the third, fourth and fifth toes are in full contact with ground level 55. However, the hallux 48 is shown elevated and twisted relative to the ground level 55 since the inside column of the foot has not completely unwound. Furthermore, the axis 56 running through the head 23 of the talus 24 now forms approximately a 10 degree angle with respect to the ground level 55. This change in rotation of axis 56 represents the twist remaining in the talar head 23, as it too did not completely unwind. For one skilled in the art, it will be appreciated that the degree of twist of the medial column of a foot having Rothbart's Foot Structure can vary depending on an individual's degree of deformity.

The timing of the lower limb bud's untwisting process explains the pathoembryological cause of both Rothbart's Foot Structure and clubfoot deformity. As indicated by G. L. Streeter and indicated above, the leg and foot untwist proximal to distal. See, Streeter, GL. "Developmental horizons in human embryos." *Contributions to Embryology*, Vols. 21, 32, 34. Washington D.C. Carnegie Institution of Washington, 1945, 1948, 1951. It does so in a temporally contiguous pattern, as follows: femur, tibia, calcaneum, and finally talus. If the untwisting process prematurely ends at the level of the calcaneum, this condition is called clubfoot deformity. If the untwisting process prematurely ends at the level of the talus, this condition is Rothbart's Foot Structure. Skeletal studies by Sewell, Olivier and Straus have demonstrated that heel bone supinatus is a component of the clubfoot deformity. See Olivier G. *Formation du Squelette des membres*. Pages 145–189. Paris, vigot Freres, 1962; and Straus, WL Jr. "Growth of the human foot and its evolutionary significance." *Contrib Embryol* 19:95, 1927. The inventor notes that in a differential diagnosis of the adult foot, when clubfoot deformity is ruled out, heel bone supinatus is concurrently ruled out. That is, heal bone supinatus cannot exist by itself. Recent clinical studies by the inventor and other clinical studies have allowed the inventor to first conclude that Rothbart's Foot Structure can exist alone or as part of a clubfoot deformity.

Additionally, Rothbart's Foot Structure has a dramatic effect on the relative length pattern between metatarsals 1 and 2. The retained twist within the talar bone elevates, twists, and proximally displaces the first metatarsal bone (similar to bowleggedness shortening the tibia). Radiographically, the first metatarsal appears 10–20 mm shorter than the second metatarsal. D J Morton was the first to clinically identify and publish on a short first metatarsal. See Morton, D J. *The Human Foot. Its Evolution, Physiology and Functional Disorders*. Columbia University Press, New York, 1935. However, Morton failed to recognize Rothbart's Foot Structure, i.e., the elevated and twisted displacement of the medial column of the foot. More recently, Janet Travell has linked Rothbart's Foot Structure to the "activation and perpetuation of trigger points." It is these trigger points that lead to chronic musculoskeletal symptoms, including knee, hip and back pain.

The accumulative data from the above mentioned skeletal and clinical studies indicates that the primary cause of hyperpronation is Rothbarth's Foot Structure. Furthermore, it is believed that the diagnosis of Rothbart's Foot Structure, in most cases, precludes heel bone supinatus. Thus, wedging the heel bone or supporting the arch to treat Rothbart's Foot Structure is mechanically inefficient and only partially effective. Review of the biomechanical literature reveals that this is a common practice in treating hyperpronation. Although wedging the heel bone does decrease the observed secondary hyperpronation generated at heel contact, it does not address the primary hyperpronation generated at toe-off during gait. Furthermore, since heel bone supinatus is rarely seen in the adult foot, wedging the heel bone is avoided.

In differentiating Rothbart's Foot Structure from other structural anomalies, it is important to remember that the retained twist in the talus effects the medial column of the foot. It does not impact the heel bone, lateral column of the foot or metatarsals 2–5. As a result, it is believed that the most effective way to attenuate hyperpronation is to support the medial column of the foot in its anatomical neutral position. Thus, the present invention is directed to a foot support system that effectively builds the ground up to the medial column of a foot exhibiting Rothbart's Foot Structure, thereby supporting the foot in its anatomical position so that the foot does not inwardly collapse or hyperpronate.

Figure 5:
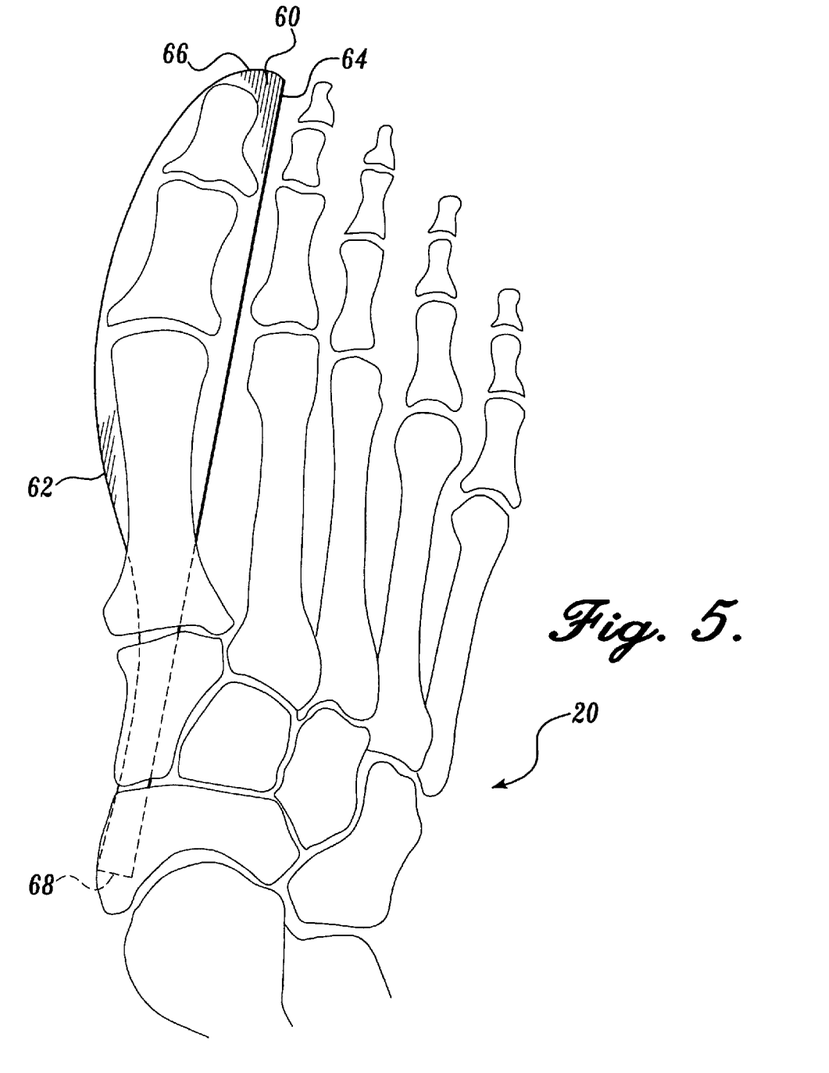
FIG. 5 is a top view of a foot depicting a foot support system according to the present invention underlying a portion of the foot.
Figure 6:
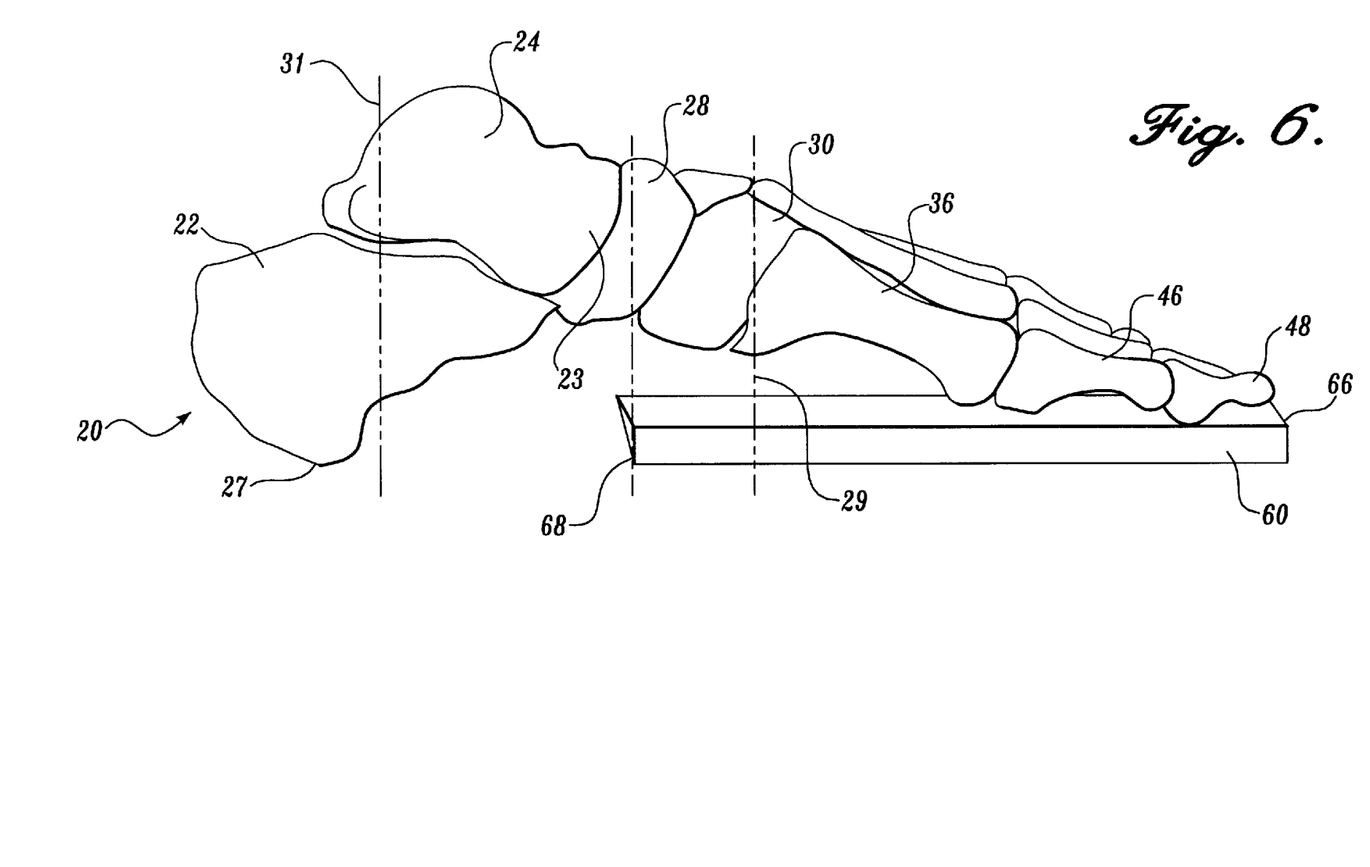
FIG. 6 is a side view of the foot support system of the present invention positioned underneath the medial column of a foot.

FIG. 5 illustrates a top view of a foot support system 60 underlying a portion of foot 20. Foot support system 60 is an elongate bed upon which a portion of the foot 20 rests which includes an inner edge 62, an outer edge 64, a front edge 66, and a back edge 68. The foot support system 60 is positioned underneath the medial column of foot 20 and extends from the hallux 48 to the navicular 28. From a side view of the support system 60 underlying the medial column of the foot 20, as shown in FIG. 6, the foot support system 60 extends from an anterior end of the hallux 48 to a position under the navicular 28. Preferably, the front edge 66 is coincident with the anterior end of the hallux 48, and the back edge 68, although lying under the navicular 28, is coincident with the anterior portion of the talus 24, defined by the talar head 23. However, it will be appreciated by one skilled in the art that the front edge 66 may also lie in a position anterior to the hallux 48, while the back edge 68 may lie in a position posterior to the first metatarsal 36 but anterior to a plantar surface 27 of the calcaneus 22, so that heel wedging is prevented. More specifically, as shown in FIG. 6, the back edge 68 may lie in along or between a reference line 29 at the posterior end of the first metatarsal 36 to a reference line 31 at the anterior end of the plantar surface 27 of the calcaneus 22.

As shown in FIG. 5, the inner edge 62 is positioned along and follows the contour of the medial side of the foot 20. The outer edge 64 lies longitudinally in a zone adjacent to a lateral margin of the hallux 48, the proximal phalanx 46 and the first metatarsal 36 and a medial margin of the phalanges 47 of the second toe and the second metatarsal 38, and does not significantly elevate the phalanges 47 of the second toe, the second metatarsal 38 or the intermediate cuneiform 32. Elevating the phalanges of the second toe, the second metatarsal, and the intermediate cuneiform by 3 millimeters or greater is considered significant. Preferably, the outer edge 64 lies along the lateral margin of the hallux 48, the proximal phalanx 46 and the first metatarsal 36.

Figure 7:
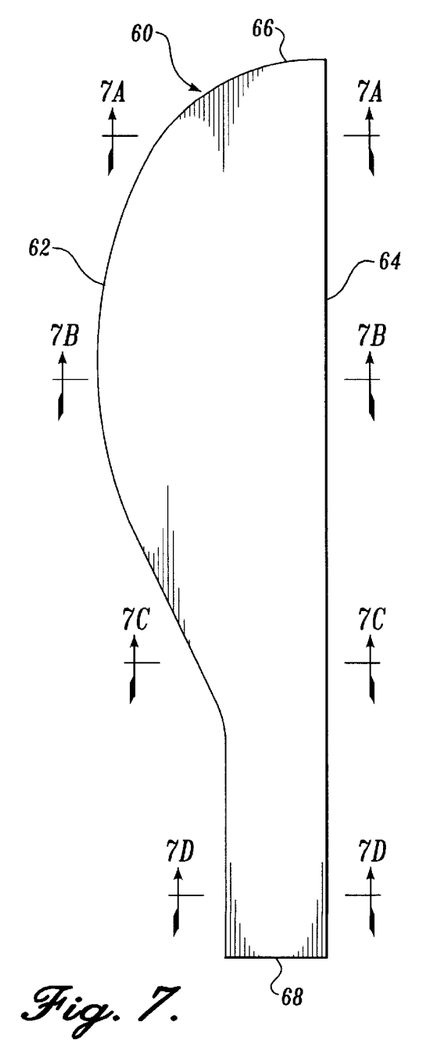
FIG. 7 is a top view of the foot support system of the present invention showing several cross-sectional portions.
Figure 7A:
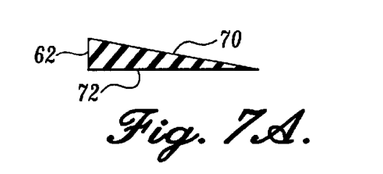
FIG. 7A is a cross-sectional view of the foot support system of the present invention taken along line 7A—7A of FIG. 7.
Figure 7B:
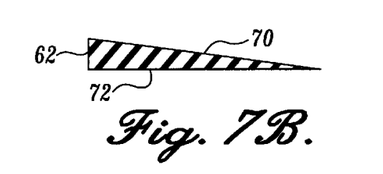
FIG. 7B is a cross-sectional view of the foot support system of the present invention taken along line 7B—7B of FIG. 7.
Figure 7C:
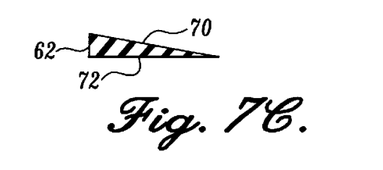
FIG. 7C is a cross-sectional view of the foot support system of the present invention taken along line 7C—7C of FIG. 7.

FIG. 7 is a top view of the foot support system 60, and FIGS. 7A, 7B, 7C and 7D are cross-sectional views of the foot support system 60 taken respectively along lines 7A—7A, 7B—7B, 7C—7C, and 7D—7D of FIG. 7. As shown in FIGS. 7A, 7B, 7C, and 7D, the foot support system 60 also includes an upper surface 70 on which the foot 20 rests and a lower surface 72. The foot support system 60 further includes a vertical component such that when the foot support system 60 is positioned underneath the foot, the medial column of the foot is supported in an elevated position relative to the remainder of the foot.

More particularly, the foot support system 60 decreases in thickness from the inner edge 62 to the outer edge 64 such that the upper surface 70 slopes downwardly from the inner edge 62 to meet the lower surface 72 at the outer edge 64. Preferably, the upper surface 70 slopes downward linearly, such that the foot support system 60 is wedge-shaped. However, it will be appreciated that the upper surface 70 can also slope downward in a concave, convex or stepped fashion. Furthermore, although the upper surface 70 preferably slopes downward to meet the lower surface 72 at the outer edge 64 such that the outer edge 64 has no vertical component, it will be appreciated that the upper surface 70 can also slope downward to the outer edge 64 without meeting the lower surface 72 such that the outer edge 64 has some thickness.

Figures 8, 9:
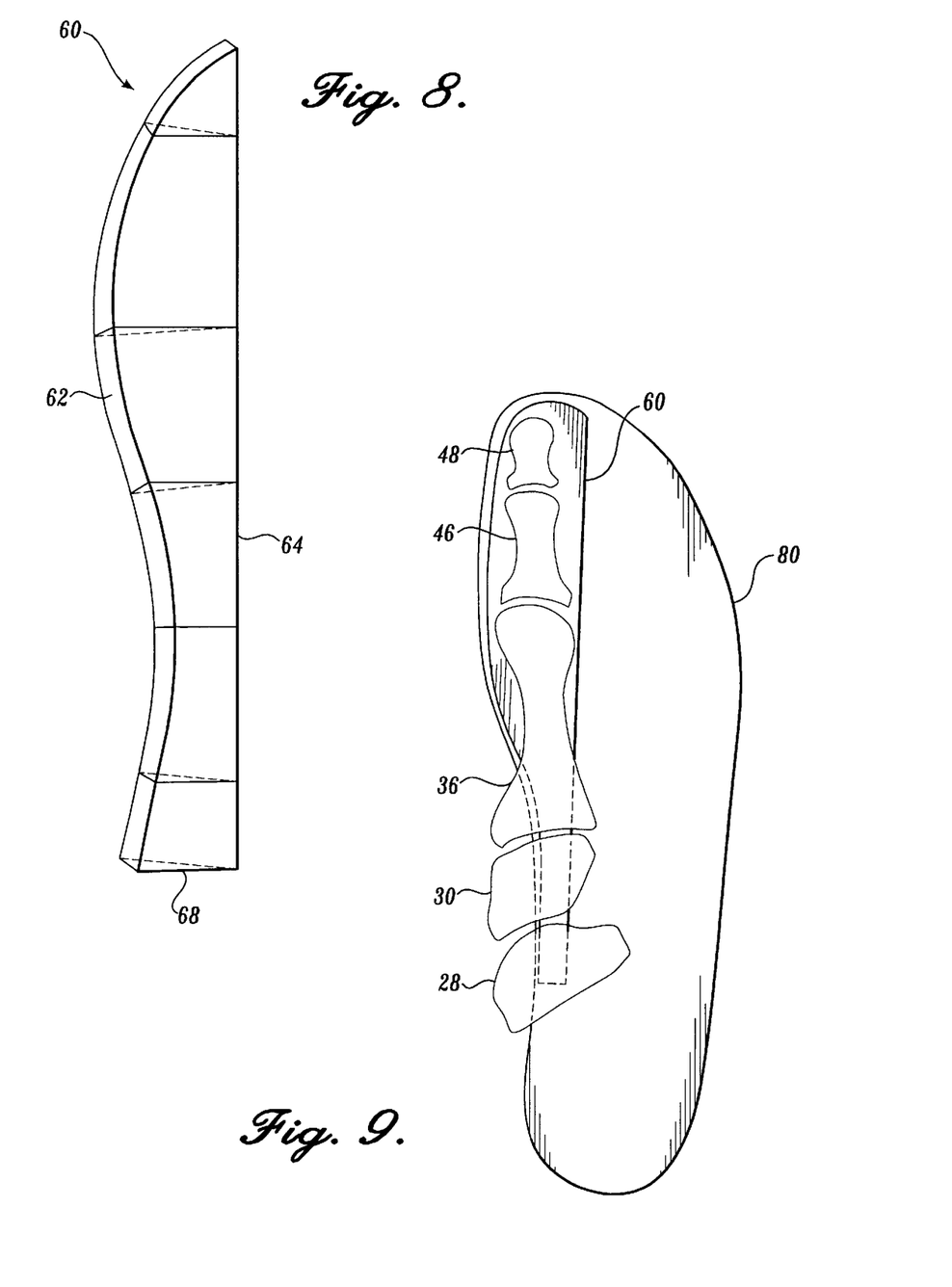
FIG. 8 is a perspective view of the foot support system of the present invention.
FIG. 9 is a top view of a foot support system of the present invention underlying a portion of a foot and positioned on top of a plate.

As shown in a perspective view of the foot support system 60 in FIG. 8, the thickness or height of the inner edge 62 of the foot support system 60 is uniform. However, it will be appreciated that, besides sloping downwardly from the inner edge 62 to the outer edge 64 of the foot support system 60, the upper surface 70 can also slope downwardly or taper as it extends forward toward the front edge 66. Furthermore, the upper surface 70 can, alternatively or additionally, slope downwardly or taper as it extends back toward the back edge 68.

Figure 7D:
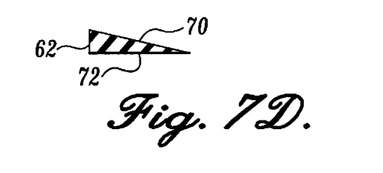
FIG. 7D is a cross-sectional view of the foot support system of the present invention taken along line 7D—7D of FIG. 7.

As shown in both FIGS. 7 and 8, the foot support system 60 varies in width, with the widest portion of the foot support system 60 underlying the proximal phalanx and the distal end of the first metatarsal 36. As the foot support system extends from its position under the proximal phalanx to the front edge 66 and to the back edge 68 of the foot support system 60, the width narrows due to the contoured shape of the medial side of the foot. As shown in FIGS. 7A, 7B, 7C and 7D, since the thickness or height of the foot support system 60 is uniform along the inner edge 62, the slope of the upper surface 70 varies depending upon the width of the lower surface 72 of the particular cross-section. In particular, in the wedge-shaped cross-section taken from the widest portion of the foot support system, shown in FIG. 7B, the slope of the upper surface 70 decreases more gradually than the slope in the cross-section taken from the narrowest portion of the foot support system as shown in FIG. 7D.

FIG. 9 illustrates a top view of the foot support system 60 positioned underneath the hallux 48, the proximal phalanx 46, the first metatarsal 36, the medial cuneiform 30 and the navicular 28 and further positioned on top of a plate 80. Plate 80 is shaped such that it follows the outer contour of the foot. Preferably, the foot support system 60 is an orthotic for wearing in a shoe, where plate 80 represents an interior bed of the shoe. However, it will be appreciated that the foot support system 60 and the plate 80 can be an integrated unit such that together they form an insole for inserting within the shoe. If the support system is incorporated into an insole, the plate 80 has no vertical rise in any area of the plate. Rather, plate 80 is flat and has a uniform thickness. Furthermore, plate 80 can be positioned either on top of or underneath the foot support system 60. Regardless, the plate's main function, in this instance, is to maintain the proper fit between the foot and the foot support system 60.

In another alternative embodiment, the foot support system 60 is built into a shoe having a shoe bed, such that the shoe bed incorporates the foot support system 60 therein. In this embodiment, the plate 80 and foot support system 60, as an integrated unit, represent the shoe bed of the shoe incorporating the foot support system 60. Since shoes are built using a last around which the shoe is formed, a shoe incorporating the foot support system 60 is preferably made with a last specially designed for creating the foot support system 60 in the shoe bed.

Figures 10, 10A, 10B, 10C, 10D:
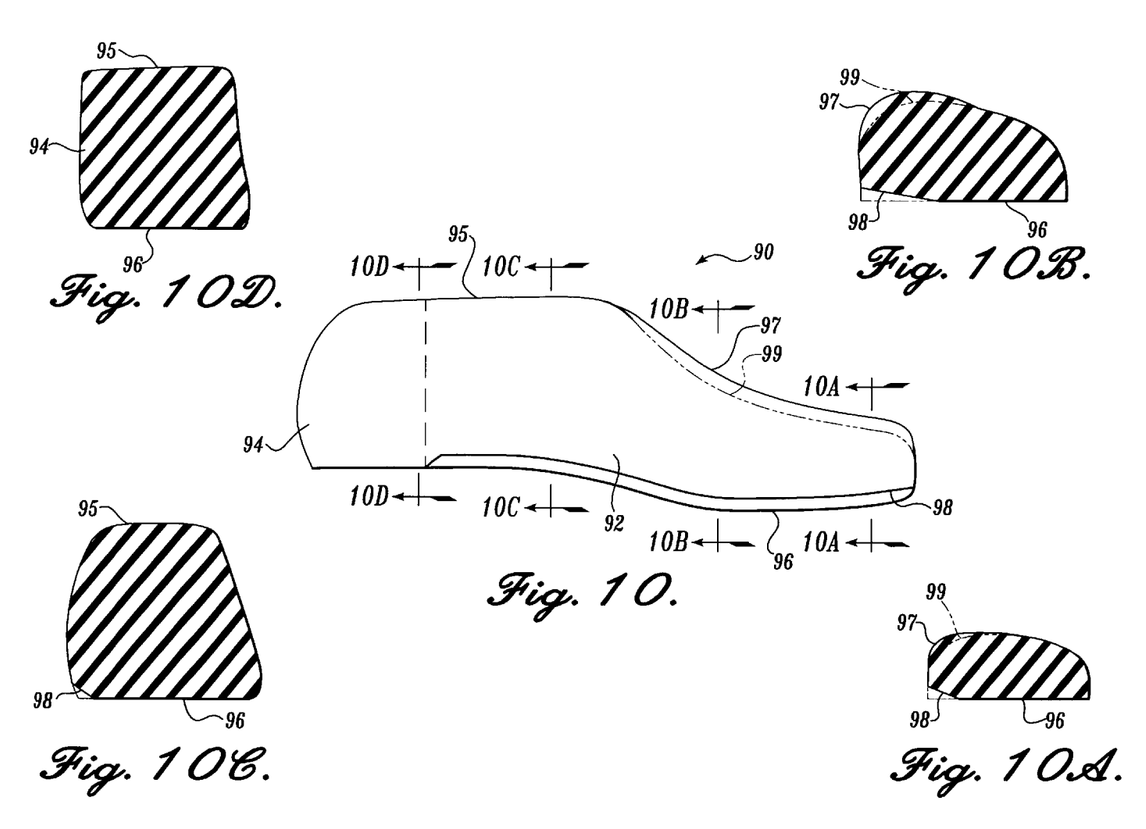
FIG. 10 is a side view of a last for making shoes incorporating the foot support system according to the present invention.
FIG. 10A is a cross-sectional view of the last of the present invention taken along line 10A—10A of FIG. 10.
FIG. 10B is a cross-sectional view of the last of the present invention taken along line 10B—10B of FIG. 10.
FIG. 10C is a cross-sectional view of the last of the present invention taken along line 10C—10C of FIG. 10.
FIG. 10D is a cross-sectional view of the last of the present invention taken along line 10D—10D of FIG. 10.

FIG. 10 illustrates a medial side view of a last 90 for making shoes which incorporate the foot support system 60. Last 90 is essentially the shape as a foot and includes a forefoot portion 92, a rearfoot portion 94, a top surface 95, a bottom surface 96, and an upper forefoot surface 97. The last 90 also contains a cavity that runs longitudinally and laterally underneath the medial column of the last 90 and that has the same shape as the foot support system 60, as described above. Furthermore, for purposes of the following discussion, the rearfoot corresponds to the plantar portion of the heel and the forefoot corresponds to the remainder of the foot.

Figure 11:
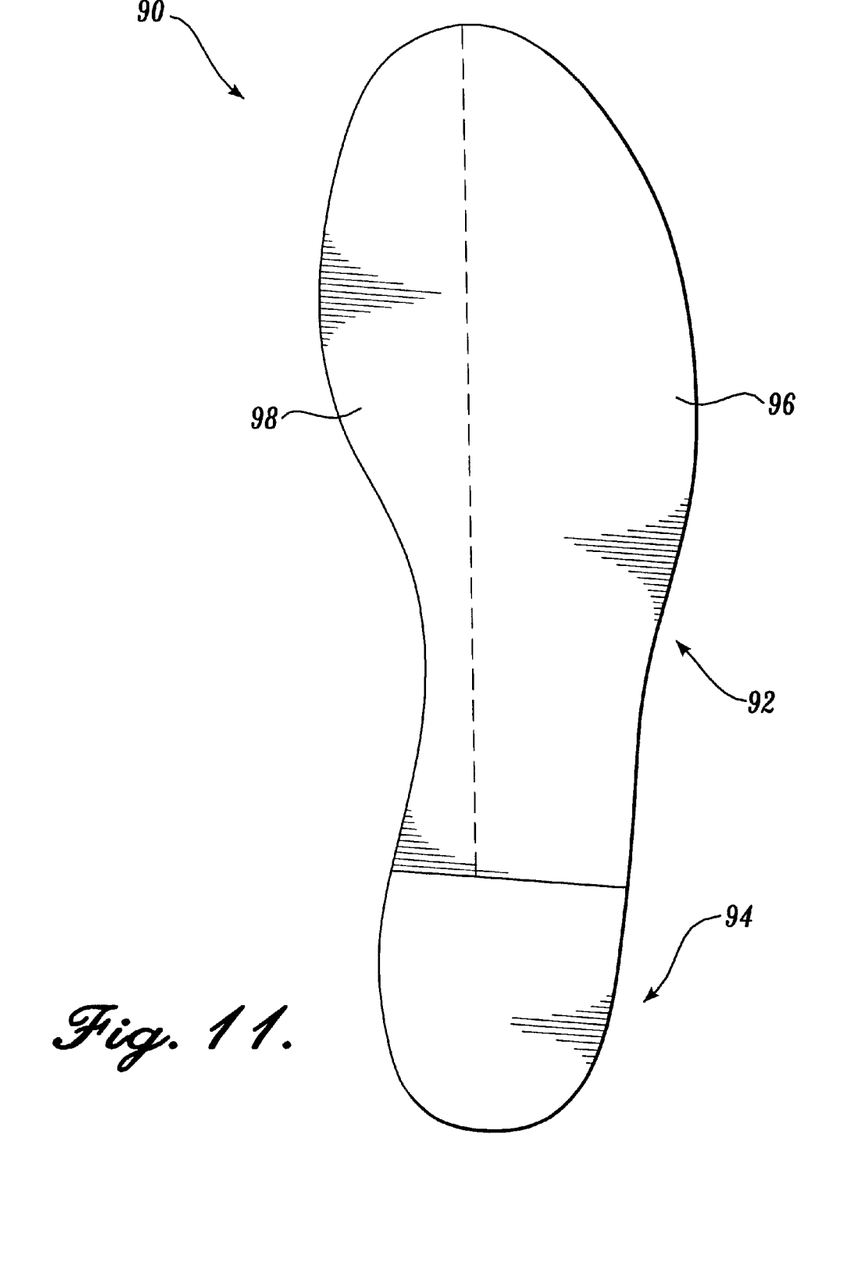
FIG. 11 is a plan view of a bottom surface of the last of the present invention.

As shown in FIG. 11 in a bottom view of last 90, the bottom surface 96 has an inner edge portion 98 which corresponds to the location of the cavity. The inner edge portion 98 extends from the front of the forefoot portion 92 to a position between the location of the navicular and the back of the forefoot portion 92, but does not extend into the rearfoot portion 94 which corresponds to the plantar portion of the heel. FIG. 11 illustrates the inner edge portion 98 extending from the front to the back of the forefoot portion 92. Furthermore, the inner edge portion 98 of the bottom surface 96 is elevated with respect to the remainder of the bottom surface, so as to adjust for the cavity corresponding to the foot support system 60. More particularly, the bottom surface 96 laterally slants downward across the inner edge portion 98 beginning at the medial side of the last.

As shown in FIG. 10A in a cross-sectional view taken along line 10A—10A of FIG. 10, the inner edge portion 98 of the bottom surface 96 of the last 90 slopes downwardly from the medial side of the last to a longitudinal position where it meets the remainder of the bottom surface 96. This longitudinal position lies in a zone adjacent to the lateral margin of the phalanges of the first toe and the first metatarsal and the medial margin of the phalanges of the second toe and the second metatarsal, as described above. Also as similarly described above in reference to the foot support system 60, the inner edge portion 98 of the bottom surface 96 can be downwardly sloped in a linear, convex, concave, or other similar manner.

In a last for making a shoe that does not incorporate the foot support system 60, the bottom surface of the last in any cross-section taken from the medial to the lateral side of the last, other than in the inner arch section, is substantially flat. However, in a last for making a shoe incorporating the foot support system of the present invention, any cross-sections taken from the medial to the lateral side of the forefoot portion 92 of the last 90 illustrate a downwardly sloped inner edge portion 98 of the bottom surface 96. Thus, when the shoe is formed around the last, the shoe contains a foot support system 60 as described above for supporting the medial column of the foot, including the hallux, the proximal phalanx, the first metatarsal, the medial cuneiform, and the navicular.

Additionally, in the last of the present invention as shown in FIG. 10A, the upper forefoot surface 97 along the medial column of the last 90 extends outwardly from an upper forefoot surface 99, representing the upper forefoot surface of a last which does not incorporate the foot support system 60. The upper forefoot surface 97 along the medial column of the last extends outwardly in order to make more space for the inner column of the foot since the bottom surface 96 of the last of the present invention is elevated along the medial side of the last.

FIG. 10B illustrates a cross-section of the last 90 taken along line 10B—10B on the forefoot portion of the last shown in FIG. 10. As shown in FIG. 10B, the inner edge portion 98 of the bottom surface 96 of the last 90 slopes downwardly as described above. However, since the width of the inner edge portion 98 varies from the distal end to the proximate end of the forefoot portion of the last and since the height of the cavity along the medial side of the last is preferably uniform, the slope of the inner edge portion varies, also as described above with respect to the foot support system 60. As shown in FIG. 10B, the slope of the inner edge portion 98 of the bottom surface of the last is more gradual than the slope shown in FIG. 10A since the cross-section taken along line 10B—10B is taken across a wider part of the inner edge portion 98 of the last. Furthermore, the upper forefoot surface 97 along the medial column of the last again extends outwardly from the upper forefoot surface 99 of the last which does not incorporate the foot sport system 60 in order to make more space for the inner column of the foot.

FIG. 10C illustrates a cross-section of the last 90 taken along line 10C—10C of the last shown in FIG. 10. As shown in FIG. 10C, the inner edge portion 98 of the bottom surface of the last again slopes downwardly as described above. However, in this instance, the slope is steeper as the width towards the proximate end of the inner edge portion is narrower. The top surface 95 is substantially flat and does not need to be outwardly extended as compared to the top surface of a last not incorporating the foot support system 60 since the top surface 95 corresponds to the location in which a foot is inserted into a shoe made from this last.

FIG. 10D illustrates a cross-section of the last 90 taken along line 10D—10D on the rearfoot portion 94 of the last 90 shown in FIG. 10. The bottom surface 96 of the rearfoot portion 94 is flat, as the inner edge portion 98 does not extend into the rearfoot portion 94. Furthermore, the top surface 95 of the rearfoot portion 94 is also flat since the top surface 95 corresponds to the location where a foot will be inserted into a shoe made from this last.

In any of the above applications, it will be appreciated that the required amount of vertical support in the foot support system 60 varies depending upon the degree of Rothbart's Foot Structure present in an individual's foot. The amount of vertical support required is determined by using calibrated wedges.

Figure 12:
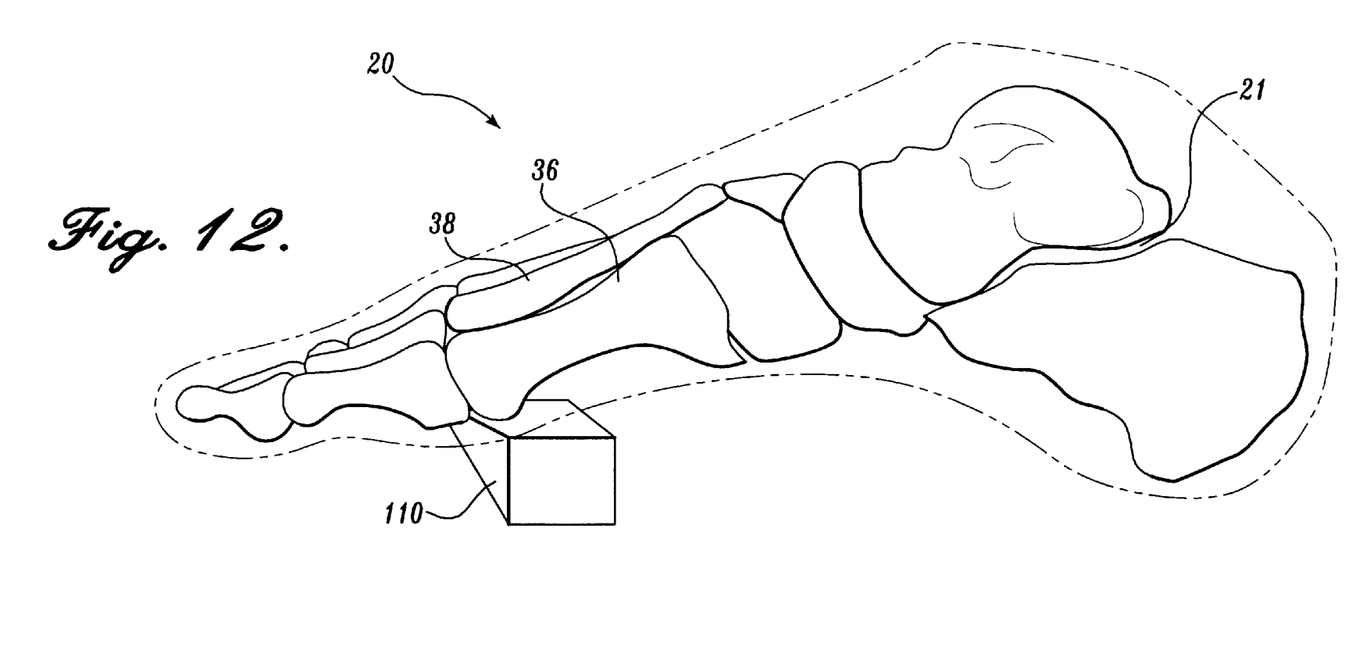
FIG. 12 is a side view of a foot depicting a calibrated wedge underneath the medial column of the foot.

FIG. 12 illustrates a calibrated wedge 110 positioned under a foot 20. While an individual with Rothbart's Foot Structure is standing, the calibrated wedge 110 is slid underneath the distal end of the first metatarsal 36, but should not be slid underneath the second metatarsal. Incremental wedging is applied to the foot until the subtalar joint 21 remains in joint congruity as the individual's weight is transferred forward to the toes. This procedure emulates the transfer of forces in the foot during late stance phase of gait. The amount of vertical support required to achieve this, represents the amount of Rothbart's Foot Structure present in that foot.

A practitioner then determines the amount of vertical support required in a prescription. This force is described in terms of millimeters of vertical support. Typically, the practitioner's prescribed vertical support should be no more than 50% of what was measured in the foot so that the body does not react negatively to the positional shift. Thereafter, based upon medical discretion, the practitioner could increase the prescription with time. The vertical support necessary to support Rothbart's Foot Structure can vary from 2 mm to 70 mm.

Additionally, it will be appreciated that the precise dimensions of the foot support system could follow a predetermined generic dimension for mass production and distribution. It has been estimated that over 95% of the adult population has some degree of Rothbart's Foot Structure. Therefore, a foot support system with a minimal degree of vertical support can be mass produced. This mass production could best be achieved using a last incorporating the foot support system as described above.

As will be readily appreciated by those skilled in the art and others, a foot support system formed in accordance with the invention has a number of advantages. First, by supporting the medial column of a foot, exhibiting Rothbart's Foot Structure, from the hallux to the navicular, the foot support system effectively supports the foot in its anatomically neutral position both statically and dynamically while walking. In particular, the foot support system directs the foot to move in a linear fashion by preventing the foot from twisting and crashing into a shoe as weight is transferred forward over the foot. Specifically in this regard, the foot support system is active during the late stance of gait, or "toe-off," where prior orthotics or foot devices have proven inactive, since it supports the hallux as well as the rest of the medial column of the forefoot. Furthermore, when the foot is maintained in this position, such that Rothbart's Foot Structure is supported, the foot does not collapse into the shoe, and thus, walking becomes easier and more comfortable. Even further, the foot support system of the present invention reduces hyperpronation of the foot, and therefore, also reduces knee and lower back problems, such as knee-knocking and swaybacks, which are commonly associated with an unstable foot structure.

While the preferred embodiment of the invention has been illustrated and described, it will be appreciated that various changes can be made therein without departing from the spirit and scope of the invention. For instance, the degree of the slope of the foot support system and thus the height of the inner edge can vary for persons with more severe cases of hyperpronation and Rothbart's Foot Structure. Furthermore, the area of the foot support system can vary according to foot size. Even further, an arch support can be used in combination with the foot support system to provide additional support when necessary.

What is claimed is:

1. A last for making a shoe having a shoe bed which incorporates a foot support system, the last similarly shaped in the form of a foot, the last including a forefoot portion, a rearfoot portion, an upper forefoot surface, and a bottom surface having an inside edge corresponding to a medical side of the last, the improvement comprising:

a cavity disposed in the bottom surface of the last, said cavity defined by an elongate inner edge portion on the bottom surface, said elongate inner edge portion extending downwardly beginning from an inside edge of the last to a longitudinal position in a zone adjacent to a portion of the last corresponding to a lateral margin of the first toe and first metatarsal to thereby form an upwardly extending cavity that in a shoe made from the last forms a foot support system for supporting primarily the first toe and first metatarsal of the foot.

2. A last for making a shoe having a shoe bed which incorporates a foot support system, the last similarly shaped in the form of a foot, the foot having a forefoot, a rearfoot, a sole, a medial side, a medial column, a first toe, a first metatarsal, a second toe, a second metatarsal, and a heel, the heel having a plantar portion, the rearfoot including the plantar portion of the heel, the first toe and first metatarsal each having a lateral margin and the second toe and second metatarsal each having a medial margin, said last comprising:

a bottom surface having an inside edge corresponding to a medial side of the last, said bottom surface having an elongate inner edge portion disposed in the forefoot of the last, said elongate inner edge portion extending downwardly beginning from the inside edge of the last to a longitudinal position in a zone substantially between the lateral margin of the first toe and first metatarsal and the medial margin of the second toe and second metatarsal, wherein said elongate inner edge portion of the bottom surface meets the remainder of the bottom surface to thereby form an upwardly extending cavity that in a shoe made from the last forms a foot support system for support primarily the first toe and first metatarsal of the foot.

3. The last of claim 2, further comprising an upper forefoot surface extending upwardly from said longitudinal position to the inside edge of the last, in order to make room in the shoe made from said last for the medial column of the foot.

4. The last of claim 2, wherein the elongate inner edge portion extends from the distal end to the proximate end of the forefoot.

* * * * *

UNITED STATES PATENT AND TRADEMARK OFFICE
CERTIFICATE OF CORRECTION

PATENT NO. : 6,212,723 B1
DATED : April 10, 2001
INVENTOR(S) : B. A. Rothbart

Page 1 of 1

It is certified that error appears in the above-identified patent and that said Letters Patent is hereby corrected as shown below:

Column 10, (Claim 1, line 5)
Line 22, "medical" should read -- medial --

Column 10, (Claim 2, line 23)
Line 56, "for support primarily" should read -- for supporting primarily --

Signed and Sealed this

Fourth Day of September, 2001

*Attest:*

*Attesting Officer*

NICHOLAS P. GODICI
*Acting Director of the United States Patent and Trademark Office*